United States Patent
Marino et al.

(10) Patent No.: US 6,960,224 B2
(45) Date of Patent: Nov. 1, 2005

(54) LAMINATED SHEETS FOR USE IN A FULLY RETRIEVABLE OCCLUSION DEVICE

(75) Inventors: Joseph A. Marino, Apple Valley, MN (US); Michael P. Corcoran, Oakdale, MN (US); Peter M. Buonomo, Shorewood, MN (US)

(73) Assignee: Cardia, Inc., Burnsville, MN (US)

(*) Notice: Subject to any disclaimer, the term of this patent is extended or adjusted under 35 U.S.C. 154(b) by 182 days.

(21) Appl. No.: 10/348,864

(22) Filed: Jan. 22, 2003

(65) Prior Publication Data

US 2004/0143292 A1 Jul. 22, 2004

(51) Int. Cl.[7] .............................................. A61B 17/08
(52) U.S. Cl. ...................................................... 606/215
(58) Field of Search ................................ 606/151, 157, 606/213–216, 232, 217

(56) References Cited

U.S. PATENT DOCUMENTS

| | | | |
|---|---|---|---|
| 3,874,388 A | 4/1975 | King et al. | |
| 5,108,420 A | * 4/1992 | Marks | 606/213 |
| 5,171,259 A | 12/1992 | Inoue | 606/213 |
| 5,334,217 A | 8/1994 | Das | 606/213 |
| 5,397,331 A | 3/1995 | Himpens et al. | 606/151 |
| 5,425,744 A | 6/1995 | Fagan et al. | 606/213 |
| 5,433,727 A | 7/1995 | Sideris | 606/213 |
| 5,451,235 A | 9/1995 | Lock et al. | 606/213 |
| 5,634,936 A | 6/1997 | Linden et al. | 606/213 |
| 5,702,421 A | 12/1997 | Schneidt | 606/213 |
| 5,709,707 A | 1/1998 | Lock et al. | 606/213 |
| 5,725,552 A | 3/1998 | Kotula et al. | 606/213 |
| 5,741,297 A | * 4/1998 | Simon | 606/215 |
| 5,904,703 A | 5/1999 | Gilson | 606/213 |
| 6,174,322 B1 | 1/2001 | Schneidt | 606/213 |
| 6,206,907 B1 | 3/2001 | Marino et al. | 606/215 |
| 6,379,368 B1 | 4/2002 | Corcoran et al. | 606/153 |

FOREIGN PATENT DOCUMENTS

| | | |
|---|---|---|
| EP | 0 362 113 | 4/1993 |
| EP | 0 541 063 | 9/1998 |
| GB | 2 269 321 A | 9/1994 |

* cited by examiner

*Primary Examiner*—Kevin T. Truong
(74) *Attorney, Agent, or Firm*—Kinney & Lange, P.A.

(57) ABSTRACT

An occlusion device having laminated polyvinyl alcohol sheets for occluding a defect. The laminated polyvinyl alcohol sheets provide an increased tear strength to the sheets that allows the device to be fully retrievable through the same catheter used to deploy it. The laminated sheets are created by obtaining thin sheets of polyvinyl alcohol foam, arranging the sheets on one another, and applying heat and pressure to laminate the sheets together.

19 Claims, 7 Drawing Sheets

LAMINATED SHEETS FOR USE IN A FULLY RETRIEVABLE OCCLUSION DEVICE

CROSS-REFERENCE TO RELATED APPLICATION(S)

This application is related to U.S. patent application entitled Articulated Center Post, Ser. No. 10/348,865, Occlusion Device Having Five or More Arms, Ser. No. 10/348,701, Septal Stabilization Device, Ser. No. 10/349,744, and U.S. patent application entitled Hoop Design for Occlusion Device, Ser. No. 10/349,118, all filed on even date herewith.

BACKGROUND OF THE INVENTION

The present invention relates to an occlusion device for use in occluding a septal wall. More specifically, the present invention relates to a fully retrievable occlusion device having occluding sheets made by laminating two or more sheets of polyvinyl alcohol foam together.

The heart is generally comprised of four chambers, the left and right atria and the left and right ventricle. Separating the left and right sides of the heart are two walls, or septa. The wall between the two atria is the interatrial septum, and the wall between the two ventricles is the interventricular septum. There are several cardiac defects which can both children and adults, including patent ductus arteriosus, patent foramen ovale, atrial septal defects (ASDs), and ventricular septal defects (VSDs).

Normally, permanently repairing septal or other cardiac defects in adults and children requires open heart surgery; a high risk, painful and costly procedure. In response to these concerns, modern occlusion devices have been developed to treat certain septal defects. Rather than surgery, these occlusion devices are small enough to be deployed by inserting a catheter into a major blood vessel and moving the occlusion device through the catheter. This type of procedure can be performed in a cardiac cathlab, and avoids much of the risks, cost, and pain associated with open heart surgery. Such occlusion devices can be used to treat a wide range of cardiac defects, including patent ductus arteriosus, patent foramen ovale, atrial septal defects, ventricular septal defects, and can be used to occlude other cardiac and non-cardiac apertures.

Occlusion devices that can be inserted via a catheter include button devices, collapsible umbrella-like structures, and plug-like devices. Occlusion devices with umbrella-like structures use a system of small metal wire arms to hold the occlusion device in place. To ensure proper seating and successful occlusion, the occlusion device must be stiff enough and have enough tension so that the occlusion device will remain in place even as the heart pulses. In addition, the occlusion device must have a high cycle life, so that it does not develop fatigue failure problems or break due to the constant flexing of portions of the occlusion device caused by the beating heart. Lastly, the device must have a suitable tactile response so that when it is deployed, the physician can "feel" whether or not the device has been successfully deployed at the defect.

Each of these design features compete with the other, making it difficult to design an occluder which adequately addresses all of them. Increasing stiffness may increase the tactile response, but may also lead to a decreased cycle life. This is because increasing the stiffness typically involves varying the shape and increasing the diameter of the wires used in occlusion devices. However, increasing the diameter of the wire to improve its stiffness or strength often reduces the cycle life because a larger diameter wire is often more brittle, and thus more susceptible to fatigue failure. Conversely, using smaller, thinner wires may result in increase fatigue life, but may also reduces the ability of the occlusion device to successfully occlude the defect, and may adversely affect the tactile response felt by the physician.

Another design challenge lies in designing sheets which attach to the wire arms. It is desired that the sheets be very thin, so that even when folded for insertion into a catheter, the occlusion device can fit into the smallest possible catheters. However, the sheets must likewise be thick enough that when the device is deployed, it provides the desired occluding effect. The sheets must also be strong enough to withstand the environment of the heart, and must be attached to the arms of the occlusion device in such a way that the sheets do not tear away from the occlusion device during passage through the catheter, or during and after implantation.

A further challenge in designing occlusion devices comes when designing the device so that it can be withdrawn if improperly deployed. Most occlusion devices are not retrievable. In instances where an occlusion device has been improperly deployed, correction of such improper deployment can often only be achieved by resorting to open heart surgery. Similarly, open heart surgery is required in instances where the occlusion device has embolized. Even if the device is partially retrievable, it may require inserting a larger catheter to accommodate removal of the occlusion device. Also, if retrieval is possible, the occlusion device is often not reusable. Rather, the first device must be removed and a second, new occlusion device must be loaded into the catheter for insertion. The result is a longer more complicated procedure and increased expense.

Thus, there is a need in the art for an occlusion device having occlusion sheets which are thin enough to allow the device to be passed through a catheter, yet strong enough to provide the desired occluding effect and remain attached to the occlusion device during deployment and insertion. There is also a need in the art for an occlusion device that can be fully retrieved through the same catheter used for deployment.

BRIEF SUMMARY OF THE INVENTION

The present invention is an improved occlusion device for occluding a defect in a septal wall. The occlusion device is comprised of a center section to which first and second fixation devices are attached. Attached to the first and second fixation devices are sheets which serve to further occlude the defect. To prevent damage to surrounding tissue, the fixation devices may be fitted with atraumatic tips. When deployed, the center section extends through the defect, and the first fixation device and first sheet are positioned on one side of the defect, while the second fixation device and second sheet are located on the other side of the defect. The first and second fixation devices are formed to bias the sheets toward the wall of the defect so that the sheets occlude the defect.

The sheets of the occlusion device are preferably formed from polyvinyl alcohol foam and have a thickness of between about 0.1 mm to 2.0 mm. To ensure that the sheets have the desired occlusion properties and are strong enough, the sheets are formed by laminating two separate sheets of polyvinyl alcohol foam to one another. The thickness of the separate sheets which are laminated together may vary, as may their shape. To laminate the sheets together, heat and pressure are applied for the desired length of time required to achieve lamination of the sheets.

When provided with such laminated sheets, the occlusion device is strong enough to be made fully retrievable. As such, it is possible to retrieve the device when only one side has been improperly deployed, when both sides have been improperly deployed, or even after the device has embolized. The device is fully retrievable through the same size catheter used for deployment of the device.

DETAILED DESCRIPTION

Figure 1:
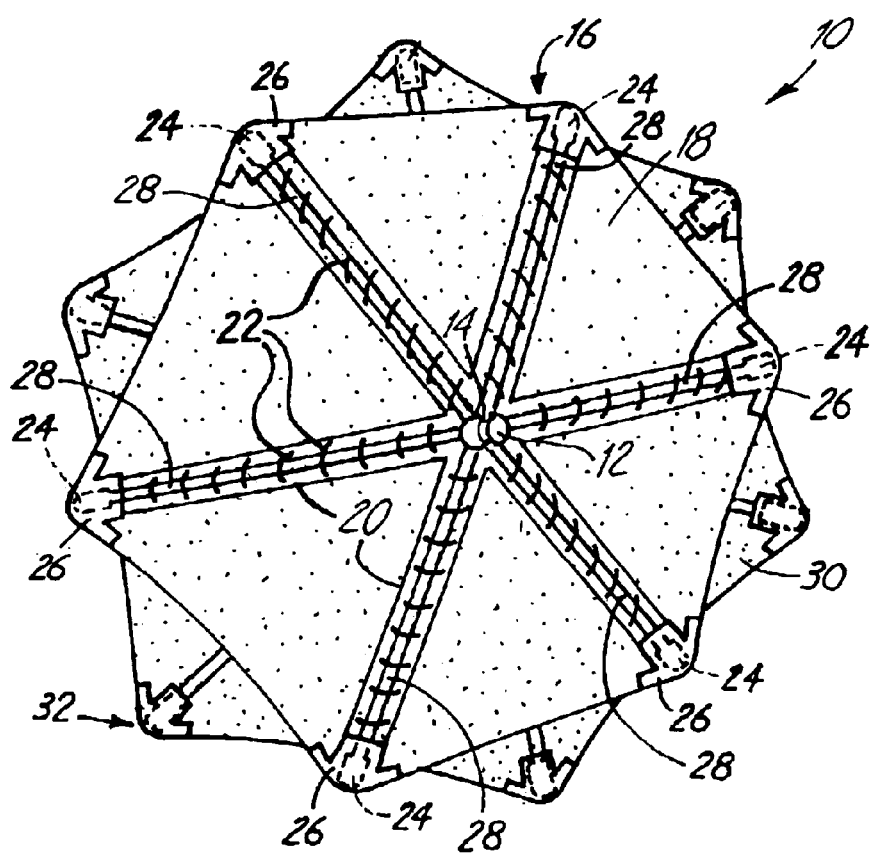
FIG. 1 is perspective view of one side of an occlusion device having laminated first and second sheets.

FIG. 1 is a top perspective view of one embodiment of an occlusion device 10. The occlusion device 10 comprises a center section 12 having a groove 14, a first fixation device 16, a first sheet 18, a first laminated area 20, sutures 22, atraumatic tips 24, and end patches 26. The first wire fixation device 16 comprises six wire arms 28, on the end of which are the atraumatic tips 24. The first laminated area 20 is located on the first sheet 18 and corresponds in shape to the first fixation device 16. The wire arms 28 are affixed to the first sheet 18 at the laminated area 20 via the sutures 22. The patches 26 cover the atraumatic tips 24. Also partially visible in FIG. 1 is a second sheet 30 and second fixation device 32.

Figure 2:
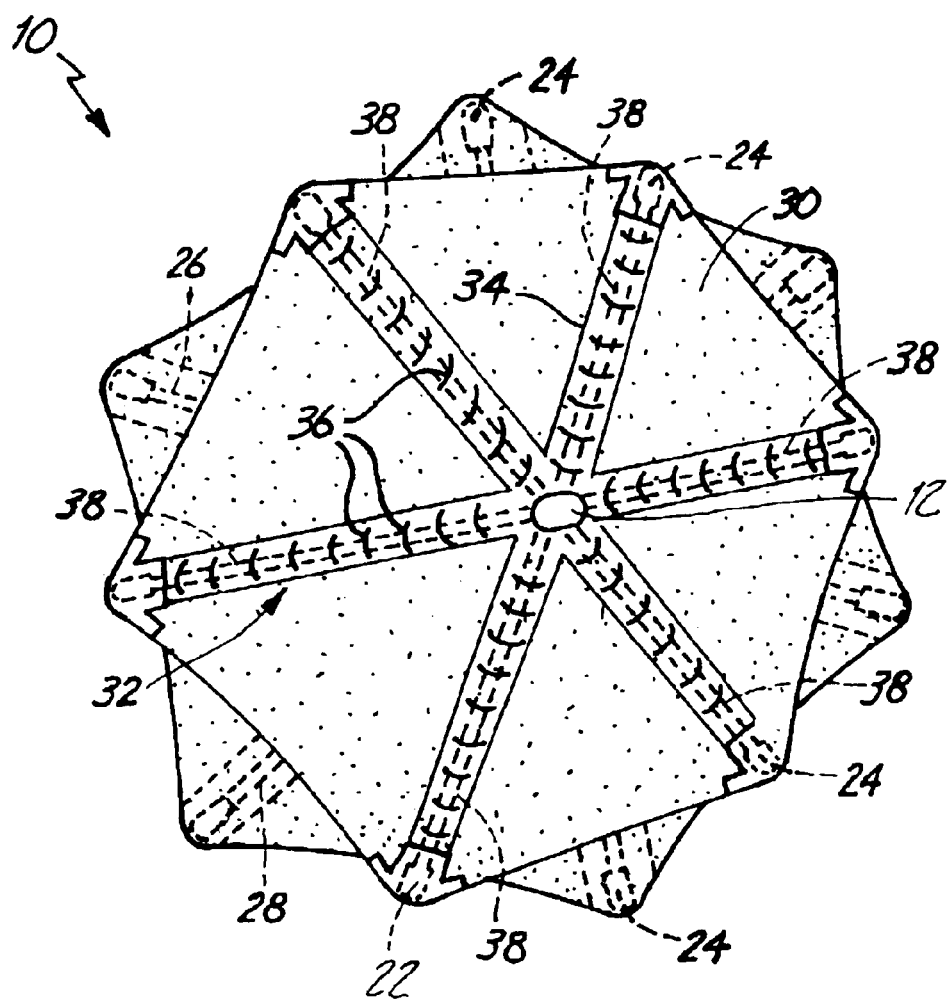
FIG. 2 is a perspective view of another side of the occlusion device having laminated first and second sheets.

FIG. 2 is a bottom perspective view of the occlusion device 10. Shown in FIG. 2 is the center post 12, second sheet 30, and second fixation device 32. The second sheet 30 comprises a second laminated area 34 and sutures 36. Similar to the first fixation device 16, the second fixation device 32 likewise comprises six wire arms 38 which terminate in atraumatic tips 24. The wire arms 38 are attached to the second sheet 30 at the second laminated area 34 via the sutures 36. Also partially visible in FIG. 2 is the first sheet 18, portions of the wire arms 28, and the atraumatic tips 24.

Unlike the first fixation device 16 which is located on an outer side of the first sheet 18, the second fixation device 32 is located on an inner side of the second sheet 30. However, the device is not so limited, and the fixation devices 16, 32 may be located on the outer side of the sheets 18, 30, on the inner side of the sheets 18, 30, or any combination thereof. In addition, though shown as having six wire arms 28, 38, the occlusion device 10 is not so limited and may comprise any number of wire arms, preferably four or more.

The first and second fixation devices 16, 32 are connected to the center post 12 using any suitable method, including crimping, welding, soldering, or adhesives. One method of connecting first and second fixation devices 16, 32 to the center post 12 is to provide the center post 12 with drill holes through which the first and second fixation devices 16, 32 extend. When connected to the center post 12 using drill holes, the fixation devices 16, 32 may additionally be crimped, welded, soldered, adhered, or otherwise attached to the center post 12 in a more permanent manner.

Connecting the fixation devices 16, 32 to the center post 12 using holes drilled through the center post 12 allows the arms 28, 38 to be formed of three wires. The three wires create the six arms 28, 38 because each wire forms two arms 28, 38 when the wire passes through the center post 12. The atraumatic tips 24 are located at the distal end of each arm 28, 38 and serve to minimize damage to the surrounding tissue. Though not shown, the center post 12 may comprise an articulation to allow the device 10 to conform to a wider variety of defects.

The sheets 18, 30 are connected to the occlusion device 10 at the center post 12 and at the first and second fixation devices 16, 32. The sheets 18, 30 may be connected to the fixation devices 16, 32 using any suitable method. When attaching the sheets 18, 30 to the fixation devices 16, 32, it is preferable to stretch the sheets 18, 30 slightly to ensure the sheets 18, 30 are pulled taut when attached to the fixation devices 16, 32. Stretching the sheets 18, 30 slightly when attaching them to the fixation devices 16, 32, ensures the sheets 18, 30 are not baggy, and also helps reduce the volume of foam needed for the device.

As shown, one method of attaching the sheets 18, 30 to the fixation devices 16, 32 is to suture the sheets 18, 30 to the fixation devices 16, 32 along the length of the arms 28, 38. Alternatively or in addition, the sheets 18, 30 may be sewn to device 10 at the atraumatic tips 24. To do so, the atraumatic tips 24 may be provided with drilled holes through which sutures can pass to sew the sheets 18, 30 to the tips 24.

The reinforcement patches 26 are placed at the end of the tips 24 and may be formed as part of the sheets 18, 30. If so, that portion of the sheets 18, 30 is folded over the tips 24 to form the patches 26. The patches 26 may be secured to the sheets 18, 30 using any suitable method, including sutures, heat treatment, or laminating. The reinforcement patches 26 serve to reinforce the foam sheets 18, 30 near the ends of the wire arms 28, 38. This reinforcement helps strengthen the sheets 18, 30 at one of the locations they are likely to tear or wear. The reinforcement patches 26 also act as a cushion between the metal tips 24 of the occlusion device 10 and the tissue surrounding the defect and provide protection to the tissue from the pressure exerted by the device 10 at the atraumatic tips 24.

The occlusion device 10 is configured to be deployed through a catheter, and the groove 14 on the center section 12 is configured to allow the occlusion device 10 to be grasped by a forceps or similar device as it is guided through the catheter. More specifically, the occlusion device 10 is constructed so that the first and second fixation devices 16, 32 are easily collapsible about the center section 12. Due to this construction, the occlusion device 10 can be folded so that the first fixation device 16 is folded upwards in the axial direction and the second fixation device 32 is folded downwards in the axial direction. The first and second sheets 18, 30 attached to the first and second fixation devices 16, 32 are also flexible, and can likewise collapse as the first and second devices 16, 32 are folded.

Once inserted into the catheter, the occlusion device 10 can be deployed across a defect to occlude it. To deploy the occlusion device 10, the catheter is positioned through the defect, and the occlusion device 10 is moved out of the catheter until the first fixation device 16 and first laminated sheet 18 unfold on a first side of the defect. The catheter is then withdrawn through the defect, and the second fixation device 32 and second sheet 30 are allowed to unfold on a second side of the defect. The sheets 18, 30 are held in place by the arms 28, 38 of the fixation devices 16, 32 and serve to prevent blood flow from one side of the defect to the other.

The occlusion device 10 is preferably made from biocompatible materials with the desired properties. More specifically, the wire fixation devices 16, 32 are preferably formed of a material that is capable of shape memory. One such suitable material is a nickel-titanium alloy, commonly called Nitinol. Nitinol is preferably used because it is commercially available, very elastic, non-corrosive, and has a fatigue life greater than that of stainless steel. Similarly, the center post 12 may be formed of platinum iridium, the atraumatic tips 24 may be formed of titanium, and any sutures 22, 36 may be formed of polypropylene, all of which are bio-compatible.

The sheets 18, 30, are comprised of a medical grade polymer in the form of film, foam, gel, or a combination thereof. One suitable material is DACRON®. A preferred material is a high density polyvinyl alcohol (PVA) foam, such as that offered under the trademark IVALON®. To minimize the chance of the occlusion device 10 causing a blood clot, the foam sheets 18, 30 may be treated with a thrombosis inhibiting material. One such suitable material is heparin.

The size of the sheets 18, 30 may vary to accommodate various sizes of defects. In some instances, it may be desirable to form the sheets 18, 30 so that they are not both the same size. For instance, one sheet and its associated fixation device can be made smaller than the corresponding sheet and its associated fixation device. This is particularly useful in situations where the occlusion device 10 is to be placed at a location in the heart which is close to other nearby cardiac structures. Making the sheets 18, 30 different sizes may assist in providing optimal occlusion of a defect, without affecting other structures of the heart which may be nearby.

To ensure the occlusion device 10 is effective at closing a septal defect even after it has been passed through a catheter, the wire arms 28, 38 are preferably subjected to a precise pre-shaping to give them a "shape memory." The pre-shaping can be done either by machining, heat treatment, or both. The shape memory helps to hold the strands together and can be used to add pre-tension to the wire arms 28, 38 so that they remember their shape even after the strong deformation that occurs when the occlusion device 10 is passed through the catheter.

In the past, occlusion devices have suffered from fatigue failures, such as cracks or breaks, due to the extreme environment the human heart poses. The human heart may pulse up to 5 billion times over its lifetime, and with each pulse, the wire fixation devices 16, 32 of the occlusion device 10 may undergo flexing or bending. This flexing and bending may eventually lead to the wires experiencing fatigue failure. To avoid fatigue failure of the fixation devices 16, 32, one embodiment of the present invention relies on making the wire fixation devices 16, 32 of stranded wire or cables. The stranded wire or cable improves the fatigue life of the fixation devices 16, 32 without increasing their size or decreasing their strength. The stranded wire or cable also improves the ability of the arms 28, 38 to be bent at extreme angles to allow the device to be inserted or withdrawn into a small diameter catheter. The atraumatic tips 24 cap the wire arms 28, 38 and can serve to prevent potential unraveling of the strands in addition to preventing damage to surrounding issue.

In addition to having improved wire arms 28, 38, the present invention also comprises unique sheets of PVA foam for occluding a defect. The sheets 18, 30 are typically obtained by slicing sheets off a block of PVA foam. When formed as a foam block, the PVA resemble a sponge and comprises many small pores. To reduce the overall bulk of the occlusion device 10 and ensure that it can fit into a small diameter catheter, it is desired to have the sheets 18, 30 as thin as possible.

However, when slicing the PVA foam into thin sheets to create the sheets 18, 30 used for the occlusion device 10, the sheets 18, 30 often contained pores that extended through the width of the sheet. These pores create many "microholes" in the sheets which allowed blood to pass through the sheets. In an effort to avoid this, sheets of PVA foam can be made thicker to reduce the holes caused by the porosity of the foam. However, when the sheets 18, 30 are made thicker, the overall bulk of the occlusion device 10 is increased, and the catheter used for the occlusion device 10 must be larger.

Another problem of forming the sheets 18, 30 from thin slices of PVA foam is that the sheets 18, 30 are not very strong. This is of particular concern when attempting to suture the sheets 18, 30 to the fixation devices 16, 32. Because the foam is very thin, and highly porous, it is very easy to tear the foam sheets when loading the occlusion device 10 into the catheter, or when trying to retrieve an occlusion device 10 back in to the catheter.

As such, the sheets 18, 30 of the occlusion device 10 comprise laminated areas 20, 34. The laminated areas 20, 34 are created by laminating two layers of PVA foam together. As such, the laminated areas 20, 34 are two-ply areas having increased strength, and lower porosity. The increased strength of the two-ply areas provides a good location for the sutures 22, 36.

By forming the sutures 22, 36 at the two-ply areas, it is less likely that the holes created by the needle or the suture thread will allow blood flow through the sheets 18, 30. Each time a suture 22, 36 is created, a needle creates two holes in the sheets 18, 30 to make the stitch. Any additional holes in the sheets 18, 30 are undesirable because such holes provide a place through which blood can flow. Making the sutures 22, 34 at the laminated areas 20, 34 reduces the likelihood that the holes will be large enough to allow blood flow across the sheet 18, 30.

In addition, suturing at the laminated areas 20, 34 results in a much stronger connection between the sheets 18, 30 and the fixation devices 16, 32. This is particularly important when the occlusion device 10 is loaded or retrieved into a catheter. When the occlusion device 10 is loaded into a catheter, or in cases when it must be retrieved back into the catheter after it has been deployed, stress is placed on the foam sheets 18, 30 at every location the sheets 18, 30 are sutured to the fixation devices 16, 32. In such instances, the sheets 18, 30 must be strong enough to withstand the pressure and stress created as the occlusion device 10 is loaded or withdrawn back into the catheter. The laminated areas 20, 34 on the sheets 18, 30 greatly increases the tear strength of the sheets 18, 30, making them much more durable during loading or withdrawal.

Figure 3:
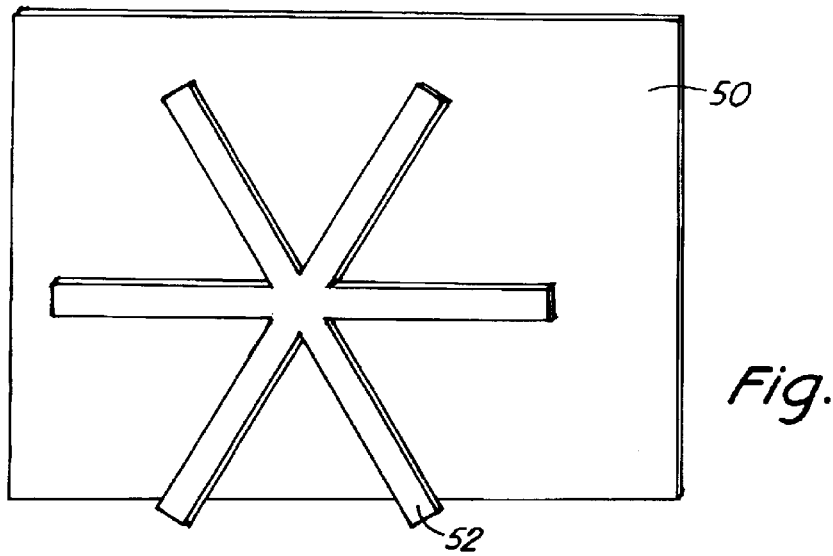
FIG. 3 is an exploded perspective view showing a first and second sheet of polyvinyl alcohol foam.

FIG. 3 is a exploded perspective view illustrating one method of forming a laminated PVA sheet for use with the occlusion device. Shown in FIG. 3 is a first sheet 50 and a second cut sheet 52. The first sheet 50 is generally a rectangle slightly larger in dimension than the size than that required for the finished sheet 18, 30. The second cut sheet 52 may be formed to correspond in shape to the desired location on the finished foam sheet 18, 30 that requires increased strength or reinforcement.

One suitable shape of the cut sheet 52 is one that corresponds to the wire arms 28, 36 of the occlusion device. Thus, the cut sheet 52 may be configured to have six arms as shown in FIG. 3, or may be configured to have any number of arms four or greater. However, the cut sheet 52 is not so limited and the cut sheet 52 may correspond in shape to any particular location on the finished sheet 18, 30 that exhibits the most stress or is most likely to tear.

When slicing the sheets 50, 52 of foam from a foam block, it is preferred that the thickness of the sheets 50, 52 range from about 0.1 mm to about 2.0 mm. More preferably, the thickness of the sheets 50, 52 is between about 0.3 mm and about 0.6 mm. One method of obtaining a first sheet 50 of PVA foam having the desired thickness is to use a microtome. However, any suitable method which can achieve the desired thickness of the PVA foam sheets may be used.

This range of thickness ensures the desired amount of strength and porosity in the foam once the sheets 50, 52 are laminated together. If the sheets 50, 52 of PVA foam are cut too thin, the sheet 50, 52 may be too flexible and even after lamination, may not have the required strength to properly occlude a defect. In addition, if the PVA foam sheets 50, 52 are cut too thin, the sheets 50, 52 may contain so many holes or pores that even after lamination, the sheet will be unsuitable for blocking blood flow. However, cutting the sheets 50, 52 too thick may result in an occlusion device that is bulkier than desired, and that requires a catheter having a diameter larger than that desired.

In addition to the thickness of the slices 50, 52, it may be desirable to choose the slices so that the slices 50, 52 are not two adjacent slices cut from the block of foam. If the slices chosen are adjacent slices, larger pores may exist that go through both sheets 50, 52. In such instances, even after the two slices 50, 52 are laminated together, the pore or hole may still extend entirely through the laminated sheet. To avoid this, the two sheets 50, 52 are chosen are preferably non-adjacent slices. In addition to choosing non-adjacent slices, it may be possible to simply rotate or offset one sheet relative to another to likewise ensure the pores or other holes in the sheets do not line up when the sheets are laminated together.

After obtaining the slices 50, 52 of foam, the next step in the lamination process is to arrange the sheets 50, 52. To do so, the cut sheet 52 is carefully placed on the rectangular sheet 50. As the cut sheet 52 is arranged on the rectangular sheet 50, it is desired that the cut sheet 52 lay as flat as possible against the rectangular sheet 50. In particular, any wrinkles are preferably removed to ensure a high quality lamination. If wrinkles exist, the wrinkles may increase the bulk of the finished sheet, making it less desirable.

After the cut sheet 52 and the rectangular sheet 50 have been arranged, the sheets 50, 52 may optionally be wetted. The sheets 50, 52 may be wetted using water or another suitable liquid. After the sheets 50, 52 are wetted, any wrinkles in either the top sheet 52 or the bottom sheet 52 may once again be removed.

Once the two sheets 50, 52 are arranged, wetted, and checked for wrinkles, the next step is to apply heat and pressure. The heat may be applied using any appropriate heat source, such as an iron. The heat source or iron preferably has a controllable temperature. A suitable temperature of the iron may range from between 100 degrees to about 180 degrees Fahrenheit. If the heat source is too hot, the PVA foam may melt. In addition, if the heat source is not hot enough, the two pieces of foam will not become laminated together. A temperature of about 140 degrees is particularly suited for laminating the sheets together.

In addition to applying heat, an amount of pressure is likewise applied to the foam sheets 50, 52. The amount of pressure may be anywhere from about 0.025 pounds of pressure to about 10 pounds of pressure and may continue for anywhere from about 1 second to about 180 seconds. This range of temperature and pressure, along with how long the temperature and pressure are applied, ensures that the two sheets 50, 52 become laminated together. At the same time, this range of temperature is not so high that the timing and pressure must be precise to avoid the danger that the sheets will scorch if not closely watched.

The ideal lamination is one where after the heat and pressure has been applied to the two sheets 50, 52 of foam, the two pieces 50, 52 can not be separated without, tearing them. However, even if the lamination is such that the foam sheets 50, 52 eventually detach from one another, the two ply sheet has still performed a useful function. In particular, when the second cut sheet 52 is in the shape of star, and is used to provide additional strength along the wire arms where the sheet is sutured to the fixation device, even if the star cut sheet 52 becomes separated from the rectangular sheet 50 at some point after suturing, the necessary strength has been provided for the sutures.

Figure 4A:
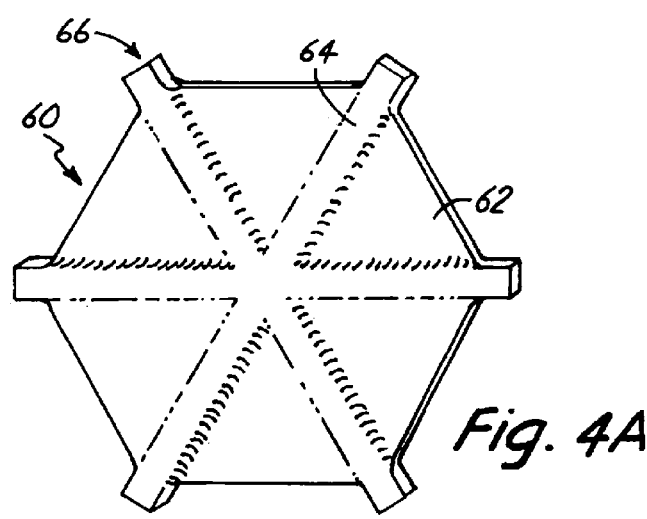
FIGS. 4a, 4b and 4c are top plan views of laminated sheets cut to the desired shape.
Figure 4B:
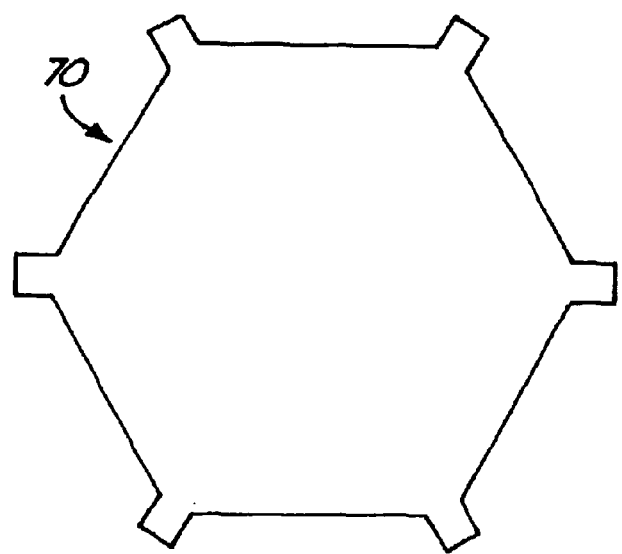
Figure 4C:
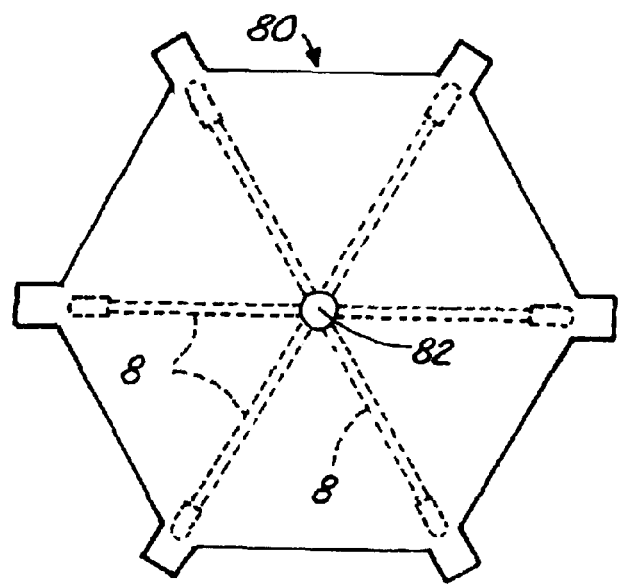

FIGS. 4a, 4b and 4c show various embodiments of laminated sheets for use in an occlusion device. Shown in FIG. 4a is a laminated sheet 60 comprising a base sheet 62 to which has been laminated a second star-shaped sheet 64. After the two sheets 62, 64 have been laminated together, the sheet 60 is cut to the final dimensions. One suitable method of cutting the sheet 60 to its final dimension and shape is to use a die cut.

As shown in FIG. 4a, the laminated sheet 60 has been cut so that the laminated sheet 60 has six sides. In addition, the laminated sheet 60 has been cut so that tab 66 extends past the corners created by each side. The tabs 66 are provided to form a locations on the laminated sheet 60 which can be overlapped when the fixation device is attached to the sheet 60. As such, the tabs 66 are one method of creating the patches 26 (FIGS. 1 and 2) that cover the atraumatic tips 24.

FIG. 4a illustrates another advantage of a laminated sheet. The sheet 60 is double thick at the star area 64, and thus has an increased strength and lower porosity in this area. The remaining area is one-ply and can be as thin as possible to provide suitable occluding ability. As a result, the foam sheet 60 is less bulky yet has the desired strength required to securely fasten it to the fixation device of the occlusion device. The reduced bulk in turn allows the occlusion device to be inserted using a smaller diameter catheter.

In addition to the configuration illustrated in FIG. 4a, the laminated area may be any configuration desired. FIG. 4b shows an alternate laminated sheet 70. In contrast to the sheet 60 in FIG. 4a, the sheet 70 in FIG. 4b does not contain a second sheet 64 in the shape of a star as shown in FIG. 4a. Rather, the laminated sheet 70 is comprised laminating two sheets of the same size together, and then cutting the laminated sheet to the desired shape.

When forming a laminated sheet 70, it may be desirable to begin with thinner slices of foam. Reducing the thickness of the sheets used to form the laminated sheet 70 reduces the finished thickness of the sheet 70. This may ensure that the bulk of the occlusion device remains in the desired range so that a catheter having the desired diameter can still be used.

FIG. 4c illustrates yet another embodiment of a laminated sheet 80. Shown in FIG. 4c is the laminated sheet 80, a center post 82, and fixation device 84. The fixation device 84 is located between two layers of foam that have been laminated together to form the laminated sheet 80.

Any suitable method may be used to form a laminated sheet 80 having an incorporated fixation device 84. For example, the laminated sheet 80 may be formed by obtaining two slices of foam, arranging the fixation device between the two slices of foam, and laminating the foam together as described above. In determining the desired thickness for the sheet 80, any suitable thickness which achieves the desired strength and occluding properties may be used. At the same time, the desired thickness of the sheet 80 must be such that the occlusion device fits in a catheter of the desired diameter.

Once the sheets have been laminated and cut to the desired shape as illustrated in FIGS. 4a–4c, a non-thrombogenic chemical, such as heparin, may be applied to the foam sheets 60, 70, 80. The heparin is preferably applied after the laminated sheets have been cut to their desired size to prevent the heparin from wearing off as the sheets are handled during manufacture. Though it may be possible to apply the heparin to the layers of PVA foam before they are laminated together, the heat may adversely affect the non-thrombogenic properties of the heparin.

Another feature of the occlusion device formed with laminated sheets 18, 30 is that the device is fully retrievable. This unique feature relating to full retrievability of the device is possible because of several features of the present invention. The first feature is the ability to obtain slices of foam that are thin enough to reduce the bulk of the sheets when moving the occlusion device through a catheter. The second feature is the ability to laminate two sheets of foam together to get a strong enough tear strength to prevent the sheets from tearing off of the fixation devices when attempting to withdraw the device back into the catheter. In addition, the lamination feature assists in reducing the bulk of the foam sheets so that the occlusion device is small enough to fit in a narrow diameter catheter.

Next, the full retrievability feature is possible because the wire arms 96, 98 are formed of stranded wire. The stranded wire arms provide the needed tension and resistance to fatigue failure. However, the stranded wire arms are also capable of being bent at extreme angles as the device is withdrawn back into the catheter. Despite being inserted as such extreme angles, the stranded wire arms are strong and flexible to withstand such deformation without breaking. Finally, the full retrievability feature is possible by designing the length of the arms of the device to allow the device to fit back inside a catheter when the arms are bent in one direction.

Figure 5:
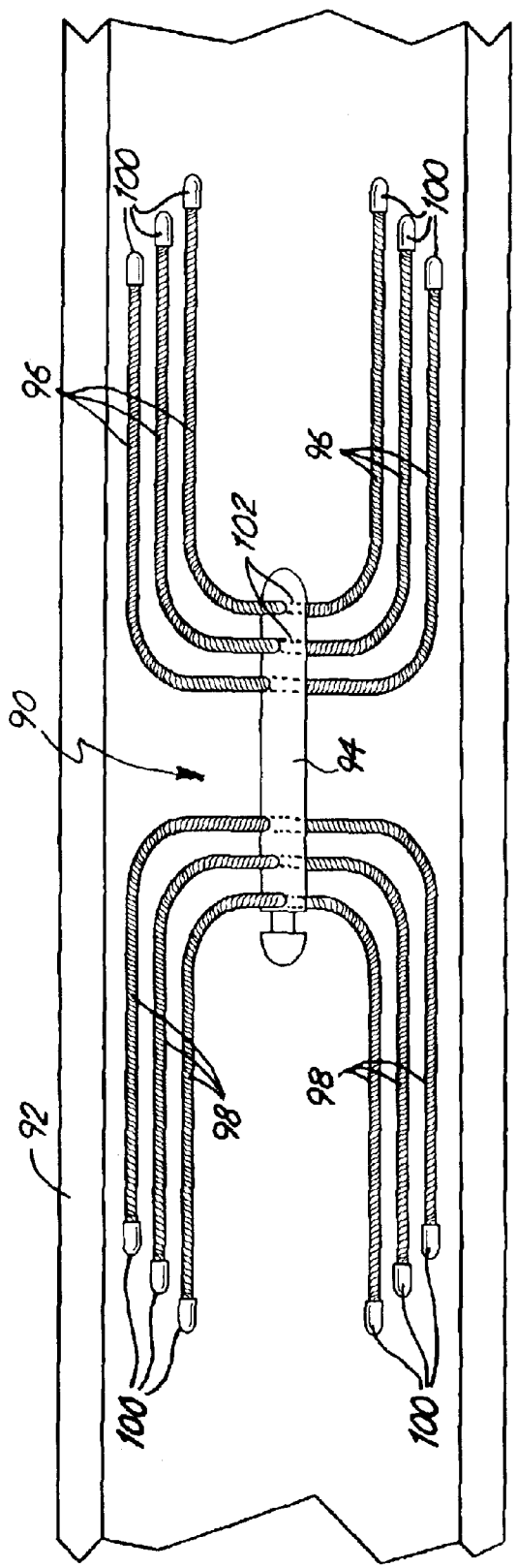
FIG. 5 is a side view of an occlusion device (with sheets not shown) collapsed within a catheter.

FIG. 5 is a side view of an occlusion device 90 inserted into a catheter 92. For the sake of clarity, the occlusion device 90 is shown without laminated sheets. The occlusion device 90 comprises a center post 94, a first set of six arms 96, a second set of six arms 98, and tips 100. The first and second arms 96, 98 are connected to the center post 94 at holes 102 drilled through the post 94. When inserted into the catheter 92, the first arms 96 are folded against the catheter 92 in the axial direction of the center post 94. Similarly, the second arms 98 are folded against the catheter 92 in an opposite direction in the axial direction of the center post 94.

When the occlusion device 90 is inserted into the catheter 92 it is important to ensure that the arms 96, 98 are not of a length that results in the tips 100 clustering at the same location. If the tips 100 all occur at the same location when the device 90 is inside the catheter 92, the device 90 will become too bulky to allow it to be easily moved through the catheter. Alternatively, a larger catheter may be required to accommodate diameters of the tips 100 if they cluster at one location.

One solution for avoiding this problem is to insert the arms 96, 98 at different locations along the length of the center post 94. When connecting the arms 96, 98 to the center post using holes 102, it is possible to space the holes to minimize the clustering of the tips 100 at one location when the arms 96, 98 are folded inside a catheter. Another way to avoid this problem is to make the arms 96, 98 of varying lengths. As is exaggerated in FIG. 6, each set of arms 96, 98 can be made of a different length, allowing all the arms 96, 98 to easily fold and fit into the catheter 92 without the tips 100 all meeting at one location. As a result, a smaller catheter can be used.

Figure 6:
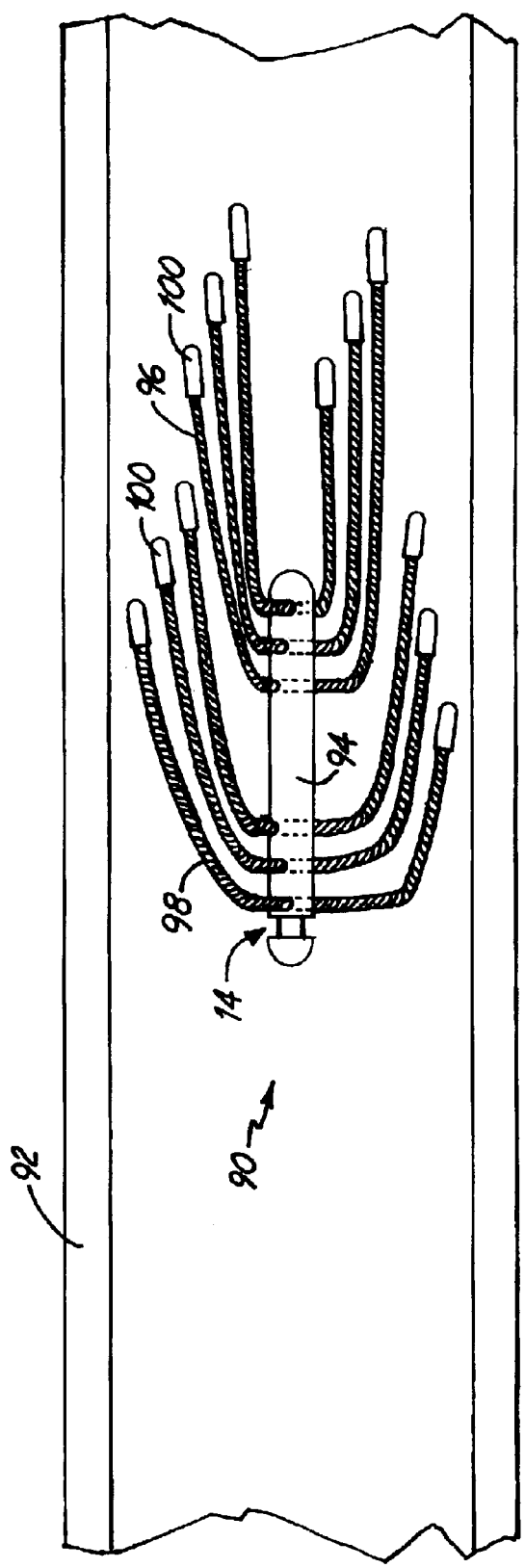
FIG. 6 is a side view of an occlusion device (with sheets not shown) withdrawn inside a catheter.

FIG. 6 is side view of the occlusion device 90 after it has been retrieved back into the catheter 92. For a variety of reasons, a physician may not be entirely happy with the placement of the occlusion device 90 after the occlusion device 90 has been deployed across a defect. In such instances, the physician may choose to retrieve the occlusion device 90 and an attempt to deploy it again. The present invention is fully retrievable in such instances.

One way to retrieve the device 90 is to grasp the device 90 at the groove 14 on the center post 12. When the device 90 is retrieved into the catheter 92 after it has been deployed, both the first arms 96 and the second arms 98 are folded in the same axial direction of the center post. In such an instance, it is likewise important to vary the length of the first arms 96 from the length of the second arms 98 so that when the device is so retrieved, the tips 100 on both the first arms 96 do not cluster at the same location as the tips 100 on the second arms 98. One way to ensure this does not occur is to make the first arms 96 a different length than the second arms 98.

Figure 7:
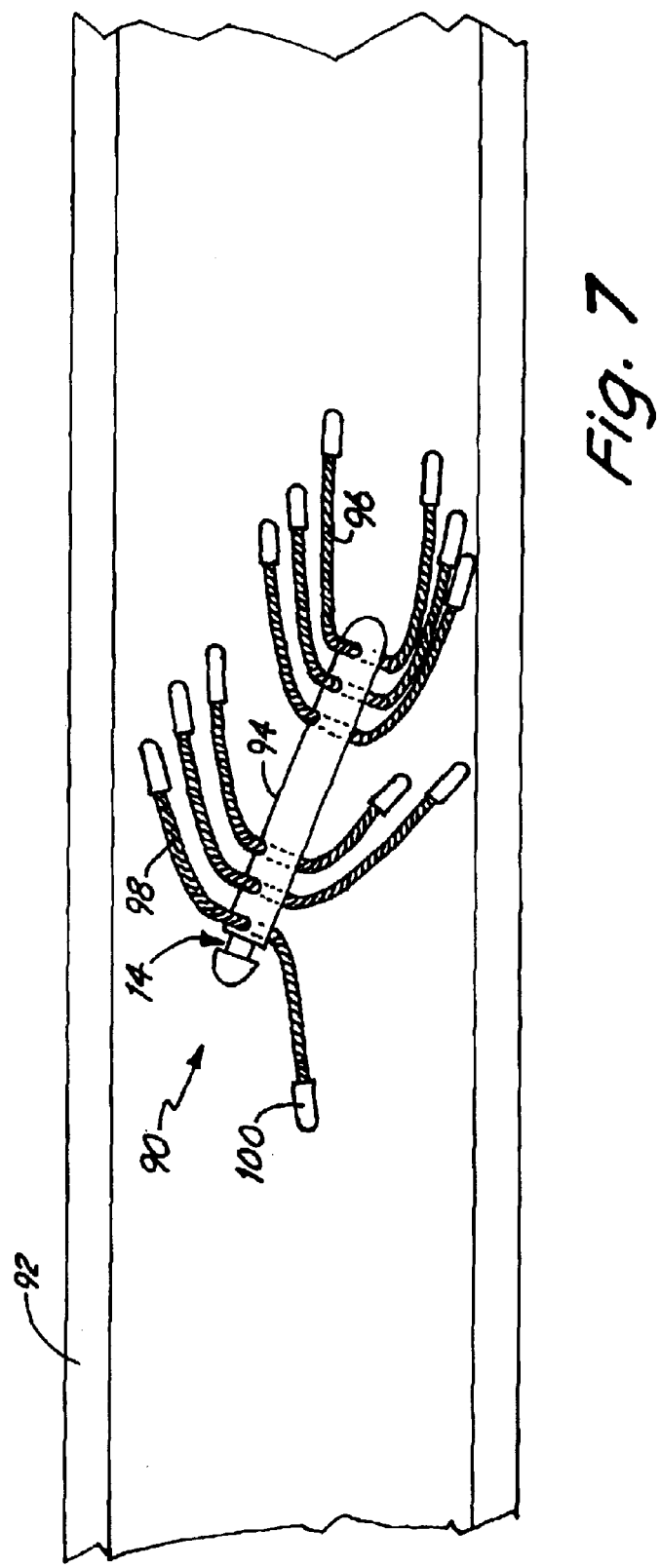
FIG. 7 is a side view of a snagged occlusion device (with sheets not shown) withdrawn inside a catheter.

FIG. 7 is yet another example of a method of retrieving the occlusion device 90 into the same catheter 92 through which it was deployed. In cases where it is difficult to grasp the center post, unique properties of the present invention allow the device to be retrieved by grasping any one of the arms at an end cap 100.

As shown in FIG. 7, after snagging an end cap 100, that arm is withdrawn back into the catheter 92. Because both the first arms 96 and the second arms 98 are flexible, as the device is pulled into the catheter 92 using one arm, the remaining arms 96, 98 fold back until they are also pulled back in to the catheter 92. In such an instance, all of the remaining arms 96, 98 fold in the axial direction of the center post 94 away from the snagged arm.

Even when retrieving the device 90 by snagging one of the arms, it is once again preferable to minimize the chance of all or several of the tips 100 on the ends of the arms 96, 98 clustering at one location. If the end caps 100 all occur at the same place in a cluster, such clusters result in the need for a larger diameter catheter to retrieve the device 90. By avoiding such clusters by controlling the length of the arms 96, 98, the device can be retrieved through the same catheter used for deployment.

Although the present invention has been described with reference to preferred embodiments, workers skilled in the art will recognize that changes may be made in form and detail without departing from the spirit and scope of the invention. In particular, any of the applicable features disclosed in related applications U.S. patent application entitled Septal Stabilization Device, Ser. No. 10/349,744, U.S. patent application entitled Articulated Center Post, Ser. No. 10/348,865, Occlusion Device Having Five or More Arms, Ser. No. 10/348,701, and U.S. patent application entitled Hoop Design for Occlusion Device, Ser. No. 10/349,118, filed on even date herewith, may be of use in the present invention. Each of these applications is hereby incorporated by reference.

What is claimed is:

1. An occlusion device that is fully retrievable, the occlusion device comprising:
   a center post;
   first and second fixation devices connected to the center post, the first and second fixation devices comprising a plurality of stranded wire support arms;
   first and second reinforced sheets attached to the first and second fixation devices, respectively; and
   end caps located at the tips of each arm and wherein the reinforced sheets comprise layers of polyvinyl alcohol foam laminated together.

2. The occlusion device of claim 1 wherein the layers of polyvinyl alcohol foam further comprise:
   a first layer; and
   a second layer laminated to the first layer to create a reinforced area on the sheet.

3. The occlusion device of claim 2 wherein the reinforced area is shaped to correspond to a shape of the first and second fixation devices.

4. The occlusion device of claim 3 wherein the reinforced sheets are attached to the fixation devices by sutures sewn at the reinforced area.

5. The occlusion device of claim 1 wherein the sheets have a thickness of between about 0.1 mm to about 2.0 mm.

6. The occlusion device of claim 1 wherein a length of the arms of the first fixation device is not equal to a length of the arms of the second fixation device.

7. The occlusion device of claim 6 wherein the arms of the first fixation device do not have equal lengths.

8. The occlusion device of claim 7 wherein the arms of the second fixation device do not have equal lengths.

9. The occlusion device that is fully retrievable through the same catheter used to deploy the occlusion device, the occlusion device comprising:
   a support frame comprising stranded wire arms; and
   a sheet connected to the support frame; wherein the sheet is reinforced to have a tear strength high enough to prevent the sheet from tearing off the support frame when the occlusion device is withdrawn into the catheter and wherein the sheet is formed of polyvinyl alcohol foam and wherein the tear strength of the sheet is provided by laminating two layers of polyvinyl alcohol foam together to form a two-ply area on the sheet.

10. The occlusion device of claim 9 wherein the two layers of polyvinyl alcohol foam comprise a first sheet and a second sheet, wherein the second sheet is shaped to correspond to a shape of the arms on the support frame.

11. The occlusion device of claim 9 wherein the tear strength of the sheet is provided by suturing the sheet to the support frame at the two ply area.

12. The occlusion device of claim 9 and further comprising atraumatic tips located at the ends of the stranded wire arms.

13. The occlusion device of claim 12 wherein the stranded wire arms are configured to allow the device to be withdrawn into the catheter by grasping any arm.

14. The occlusion device of claim 13 wherein the length of the arms is such that when withdrawn into a catheter, the atraumatic tips do not all meet at one location.

15. An improved occlusion device, the occlusion device comprising:
   a center post;
   first and second fixation devices connected to the center post;
   first and second sheets attached to the first and second fixation devices, respectively, wherein the first and second sheets comprise multiple layers of polyvinyl alcohol foam laminated together to form a multi-ply area on the sheets.

16. The occlusion device of claim 15 wherein the layers of polyvinyl alcohol foam have a thickness from between about 0.1 millimeters to about 2.0 millimeters.

17. The occlusion device of claim 16 wherein the layers of polyvinyl alcohol foam have a thickness of between about 0.3 millimeters to about 0.6 millimeters.

18. The occlusion device of claim 15 wherein the layers of polyvinyl alcohol foam comprise first sheet and a second sheet, wherein the second sheet is shaped to correspond to a shape of the fixation device.

19. The occlusion device of claim 18 wherein the first and second sheet are sutured to the fixation device at the multi-ply area.

* * * * *

UNITED STATES PATENT AND TRADEMARK OFFICE
CERTIFICATE OF CORRECTION

PATENT NO. : 6,960,224 B2 Page 1 of 1
APPLICATION NO. : 10/348864
DATED : November 1, 2005
INVENTOR(S) : Joseph A. Marino et al.

It is certified that error appears in the above-identified patent and that said Letters Patent is hereby corrected as shown below:

Column 8, Line 14, delete "without," insert --without--

Signed and Sealed this

Nineteenth Day of December, 2006

JON W. DUDAS
*Director of the United States Patent and Trademark Office*